(12) United States Patent
Martin et al.

(10) Patent No.: US 10,336,705 B2
(45) Date of Patent: Jul. 2, 2019

(54) ELECTRICALLY CONDUCTING OLIGO(PYRAZOLES)

(71) Applicant: The United States of America, as represented by the Secretary of the Navy, Washington, DC (US)

(72) Inventors: Brett D. Martin, Washington, DC (US); Scott A. Trammell, Springfield, VA (US); Jeffrey R. Deschamps, Laurel, MD (US); Jawad Naciri, Arlington, VA (US); Jeffrey DePriest, Stanley, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 83 days.

(21) Appl. No.: 15/610,324

(22) Filed: May 31, 2017

(65) Prior Publication Data

US 2017/0267644 A1    Sep. 21, 2017

Related U.S. Application Data

(62) Division of application No. 15/013,851, filed on Feb. 2, 2016, now Pat. No. 9,738,609, which is a division of application No. 14/280,002, filed on May 16, 2014, now Pat. No. 9,302,995.

(60) Provisional application No. 61/833,163, filed on Jun. 10, 2013.

(51) Int. Cl.
*C07D 231/38* (2006.01)
*C08G 73/06* (2006.01)

(52) U.S. Cl.
CPC ................... *C07D 231/38* (2013.01)

(58) Field of Classification Search
CPC .................................. C07D 231/38
USPC ............. 528/423, 482, 487, 503; 548/365.1, 548/367.4
See application file for complete search history.

(56) References Cited

PUBLICATIONS

Al-Qalaf et al; Synthesis of 5-substituted 3-amino—pyrimidines; Molecular Diversity Preservation International; 2009; Chem Abstract 151:198300 (Year: 2009).*

* cited by examiner

*Primary Examiner* — Duc Truong
(74) *Attorney, Agent, or Firm* — US Naval Research Laboratory; Stephen T. Hunnius

(57) ABSTRACT

An electrically conducting organic oligomer comprising 4-nitro-1H-pyrazole-3-yl-amine, 4-trifluoromethyl-1H-pyrazol-3-yl-amine, 4-trichloromethyl-1H-pyrazol-3-yl-amine, 4-tribromomethyl-1H-pyrazol-3-yl-amine, 4-ammonium-1H-pyrazol-3-yl-amine, 4-trimethylammonium-1H-pyrazol-3-yl-amine, 4-triethylammonium-1H-pyrazol-3-yl-amine, or 4-tripropylammonium-1H-pyrazol-3-yl-amine. An electrically conducting organic oligomer made from the steps of preparing an acidic aqueous solution with a monomer, preparing the acidic aqueous solution by mixing water with a monomer (3-amino-1H-pyrazole-4-carbonitrile), forming a solution preparing a second aqueous solution, mixing the acidic aqueous solution with the second aqueous solution, and allowing a reaction to proceed at about 40° C.

1 Claim, 24 Drawing Sheets reduced oxidized

Estimation Quality: blue = good, magenta = medium, red = rough (a)

(b)

ELECTRICALLY CONDUCTING OLIGO(PYRAZOLES)

This application claims priority to and benefits of U.S. Patent Application No. 61/833,163 filed on Jun. 10, 2013, and U.S. patent application Ser. No. 14/280,002 filed on May 16, 2014 now U.S. Pat. No. 9,302,995, and U.S. patent application Ser. No. 15/013,851 filed on Feb. 2, 2016, now U.S. Pat. No. 9,738,609 the entireties of each are herein incorporated by reference.

BACKGROUND

This disclosure concerns two novel electrically conducting organic oligomers: oligo(3-amino-1H-pyrazole-4-carbonitrile) or "oligo(AP-CN)" and oligo(4-nitro-1H-pyrazole-3-yl-amine) or "oligo(AP-NO$_2$)".

These novel electrically conducting organic oligomers have highly variable redox states and good electron-transporting properties. Our studies also show that the oligomers may be useful in applications such as polymer solar cells.

These oligomers are easy to synthesize, requiring only one step plus purification. These oligomers use inexpensive starting materials.

In photocurrent generation studies using a solar lamp and an electrolyte with a sacrificial electron donor, the oligo(AP-CN) was able to produce anodic photocurrent of magnitudes as high as 103 times that of a gold-coated electrode alone, and 43.2 times that of a fullerene-coated gold electrode. Chemical characterization of oligo(AP-CN) showed that it is a tetramer with N-linkages between repeat units. It has a high thermal stability, with an onset of thermal decomposition above 350° C.

Cyclic voltammetry and electrochemical impedance spectroscopy (EIS) studies of both oligomers showed that they are good electron conductors when in the reduced (n-doped) state. The n-dopability is quasi-reversible. This observation is further supported by circuit models that give low values for the resistor and Warburg circuit elements in when n-doped.

When partially or mostly oxidized (at 0 V or +1.2 V), the oligomers may act as p-doped conductors and semiconductors. The high electron conductivity quantified by the EIS is consistent with the observations of the large anodic (electron) photocurrents supported by the oligo(AP-CN).

Conducting polymer-based photovoltaic cells are likely to be a much less expensive alternative for solar energy than traditional inorganic photovoltaics made from such materials as silicon and gallium arsenide. Inorganics require high temperature and high vacuum processing conditions, such as molecular beam epitaxy. Up to 40% of the cost of a silicon photovoltaic cell arises from the material processing. Several types of conducting polymers, however, have been made to be liquid processable at room temperature using inexpensive methods. They can be deposited on large sheets using ink-jet printing, screen-printing, or spin-casting. As thin films they are also mechanically flexible, able to withstand bending that would fracture a silicon panel. They are also color tuneable within various ranges, so that they can be made to emit or absorb in a variety of colors.

The challenges within conducting polymer photovoltaics are low photon-to-current conversion efficiencies and short lifetimes. The current record power efficiency for a polymer photovoltaic is 3.5%, which is a full order of magnitude lower than the record power efficiency for silicon photovoltaics. However, silicon photovoltaics have benefited from about 20 years of dedicated research, whereas polymer photovoltaics are a relatively new application.

To date, the vast majority of conducting polymers are p-dopable, that is, they act as stable carriers of positive charge. In a photovoltaic cell they are often used as hole (cation or cation-radical) transporters.

Conducting polymers that are stable in their n-doped state are far less common. In this state they are able to accommodate and conduct free electrons. Such polymers are of significant value in photovoltaics as electron transporters, as well as in other applications such as organic field effect transistors (OFETs) and organic light emitting diodes (OLEDs). A common material used as the electron transporter in polymer solar cells is $C_{60}$ fullerene, either pristine or derivatized in various manners to affect electrode morphology.

Some of the few examples of n-dopable conducting and semi-conducting polymers are based on nitrogen-rich 5-membered conjugated heterocycles such as 1, 3, 4 heterodiazoles containing C, N, and S or O. A few others are based on 1, 2, 4 triazoles having two C and three N atoms. The latter are n-dopable because the ring is electron deficient and can thus be reduced into a semi-stable, electron conducting form.

The electron deficiency also results in another phenomenon—the synthesis of homopolymeric poly(triazoles) is not generally achievable by polymerization of monomeric triazole. Thus, other approaches must be used. For example, one may construct linear polyhydrazides having —CR—CR—NH—NH— repeating sequences, and then undertake ring-formation metathesis reactions that yield the triazole repeat unit.

The synthesis of these types of prior art polymers usually requires many steps, often involving the complex ring-closing reactions mentioned above.

Another, much less explored approach to the synthesis of n-dopable conducting polymers involves oxidative polymerization or oligomerization of nitrogen-rich pyrazoles with primary amines. This is done in a manner similar to the synthesis of polyaniline, wherein the amine group forms a bridge between each polymer repeat unit. One example, oligo(3-amino-1,2,4 triazole), has been synthesized and characterized as a semiconductor and as a anticorrosive for copper. This material was not n-dopable to a stable state, however, and is not an effective electron acceptor.

These oligomers disclosed herein are expected to have a significant military and commercial interest. There is a necessity for developing renewable energy sources given that world petroleum production is expected to peak within the next few years. Solar power is clean, readily available, and renewable. Silicon-based solar cells are considered to be the state of the art at present and have a relatively high efficiency, but they are expensive to manufacture.

Polymer-based solar cells are less expensive but the prior art efficiencies are low. When incorporated into these types of cells, the oligomers herein disclosed will enable increases in efficiency. This is because of the high electron transport rates of the oligomers and their versatile redox behavior.

The ease of synthesis of these currently disclosed oligomers and low cost of starting materials are further commercial advantages. These attributes also allow derivatives of the material to be produced and investigated easily and quickly.

BRIEF SUMMARY OF THE INVENTION

This disclosure concerns two novel electrically conducting organic oligomers: oligo(3-amino-1H-pyrazole-4-carbonitrile) or "oligo(AP-CN)" and oligo(4-nitro-1H-pyrazole-3-yl-amine) or "oligo(AP-NO$_2$)".

This disclosure concerns the development of a novel electrically conducting organic oligomer or polymer that has variable redox states and good electron-transporting properties, that may be useful in applications such as polymer solar cells. The oligomer or polymer is easy to synthesize (in few steps) and uses inexpensive starting materials.

DETAILED DESCRIPTION

This disclosure concerns two novel electrically conducting organic oligomers: oligo(3-amino-1H-pyrazole-4-carbonitrile) or "oligo(AP-CN)" and oligo(4-nitro-1H-pyrazole-3-yl-amine) or "oligo(AP-NO$_2$)".

These novel electrically conducting organic oligomers have highly variable redox states and good electron-transporting properties. Our studies also show that the oligomers may be useful in applications such as polymer solar cells.

These oligomers are easy to synthesize, requiring only one step plus purification. These oligomers use inexpensive starting materials.

In photocurrent generation studies using a solar lamp and an electrolyte with a sacrificial electron donor, the oligo(AP-CN) was able to produce anodic photocurrent of magnitudes as high as 103 times that of a gold-coated electrode alone, and 43.2 times that of a fullerene-coated gold electrode. Chemical characterization of oligo(AP-CN) showed that it is a tetramer with N-linkages between repeat units. It has a high thermal stability, with an onset of thermal decomposition above 350° C.

Cyclic voltammetry and electrochemical impedance spectroscopy (EIS) studies of both oligomers showed that they are good electron conductors when in the reduced (n-doped) state. The n-dopability is quasi-reversible. This observation is further supported by circuit models that give low values for the resistor and Warburg circuit elements in when n-doped.

When partially or mostly oxidized (at 0 V or +1.2 V), the oligomers may act as p-doped conductors and semiconductors. The high electron conductivity quantified by the EIS is consistent with the observations of the large anodic (electron) photocurrents supported by the oligo(AP-CN).

This disclosure concerns the development of a novel electrically conducting organic oligomer or polymer that has variable redox states and good electron-transporting properties, that may be useful in applications such as polymer solar cells. It is desired that the oligomer or polymer be easy to synthesize (in few steps) and require inexpensive starting materials.

Herein we report the synthesis and electrochemical characterization of new conjugated conducting oligomers: oligo (3-amino-1H-pyrazole-4-carbonitrile) or "oligo(AP-CN)" and oligo(4-nitro-1H-pyrazole-3-yl-amine) or "oligo(AP-NO$_2$)".

These oligomers contain nitrogen and carbon in the ratios of 1:1 and 4:3, respectively. Electrochemical studies show that the materials can adopt an n-doped state (they are good electron acceptors) and may be able to adopt a p-doped state as well.

Oligo(AP-CN)

Figure 1:
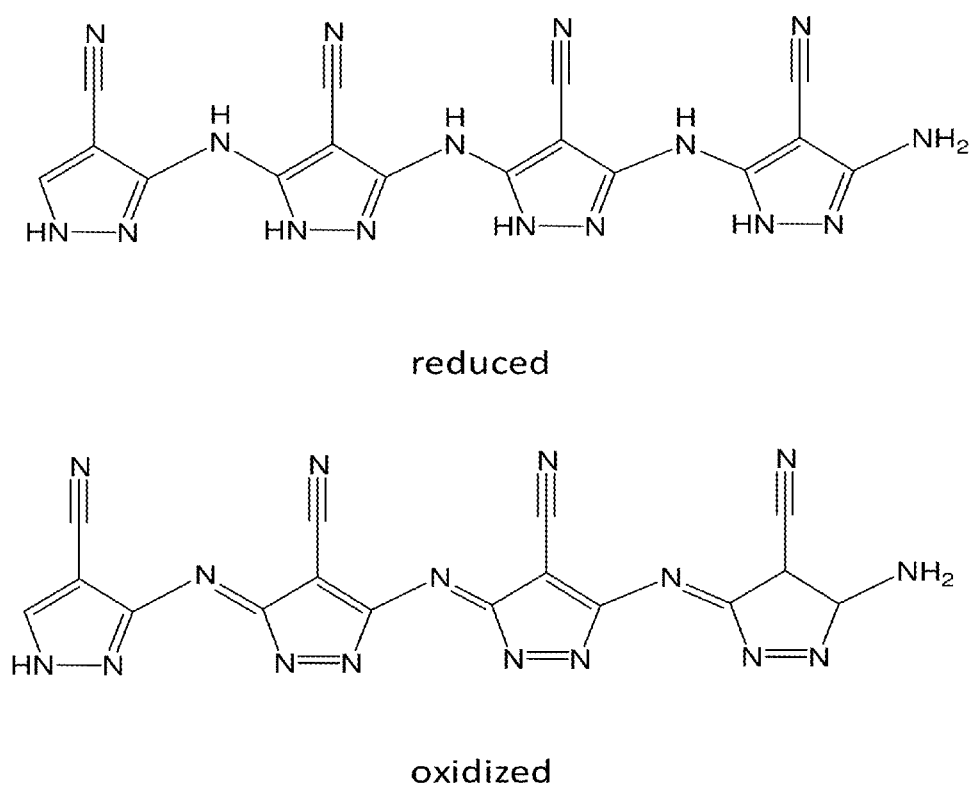
FIG. 1 illustrates Poly(3-amino-1H-pyrazole-4-carbonitrile), "oligo(AP-CN)", reduced and oxidized states.

For oligo(AP-CN), the reduced and partially oxidized forms of the material are shown in FIG. 1. The material is oligomerized at about 40° C. in a straight-forward one-step process from the starting monomer by using a stoichiometric amount of sodium persulfate in acidic solution (pH=0.5-1.0).

As the oligomerization proceeds some of the material aggregates (pi-stacking) and precipitates from solution. When the reaction is complete the rest of the oligo(AP-CN) can be readily precipitated from the solution by raising the pH to 7.0 or higher.

The oligomer is brick-red when precipitated at pH 7.1 and is dark green when precipitated at pH 10.0. It is soluble in DMF and pyridine, and the material precipitated at pH 7.1 shows strong fluorescence ($\lambda_{max}$=525 nm) when subjected to an excitation wavelength of 355 nm in DMF. UV-visible data shows that oligo(AP-CN) has a maximum absorption at 330 nm at pH 7.1.

Mass spectral data indicates that it is a tetramer of MW 426, with in-source fragmentation yielding a negatively-charged precursor ion of 385 Da. Using MS-MS, this was fragmented, giving the negative product ions of m/z 353, 265, 212, 132 and 107 Da, which were predicted from the oligo(AP-CN) chemical structure. The 107 Da was itself subjected to MS-MS, giving additional negative product ions of m/z 90, 65, 52, and 26 Da, also predicted from the chemical structure.

Figure 2:
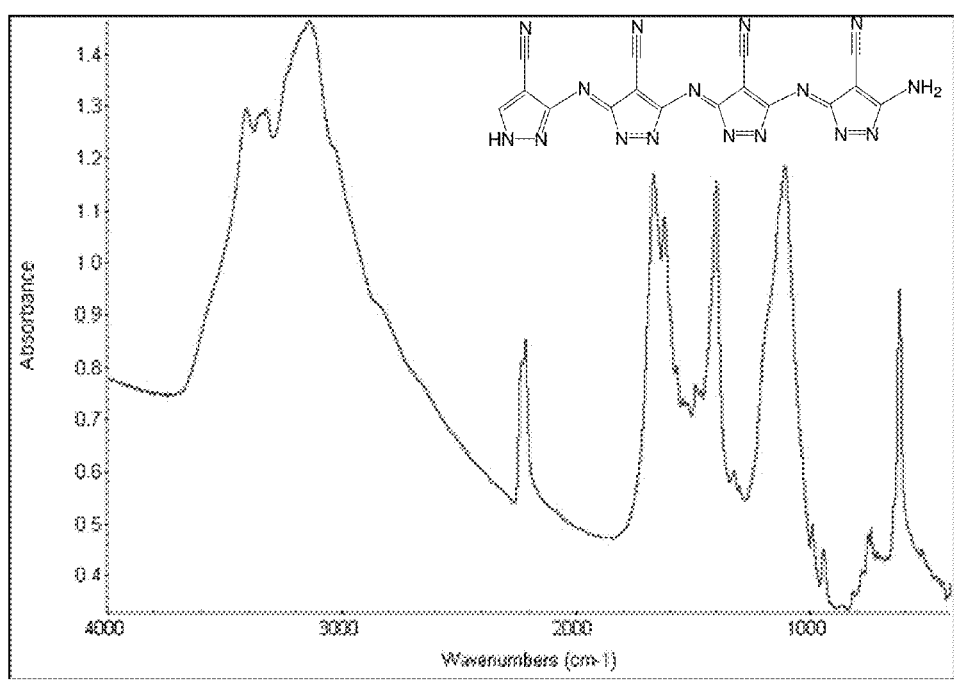
FIG. 2 illustrates FTIR spectrum of oligo(AP-CN).

FTIR data (FIG. 2) shows strong bands characteristic of secondary amines (N—H at 3317 and 3139 cm$^{-1}$), C=N/C=C conjugation (1670 cm$^{-1}$), and carbonitrile (the cyano group) in conjugation (2236 and 2219 cm$^{-1}$). Thus the cyano group remains intact as the oligomer forms.

The data also shows aromatic C=C bonds at 1406 cm$^{-1}$, C—N sigma bonds (1113 cm$^{-1}$), and the N—H sigma bond wag (616 cm$^{-1}$).

Data for the monomer shows primary amine bands that are much stronger than those of the oligomer, which is expected since it forms linkages with the neighboring pyrazole group as the oligomerization proceeds.

Figure 3:
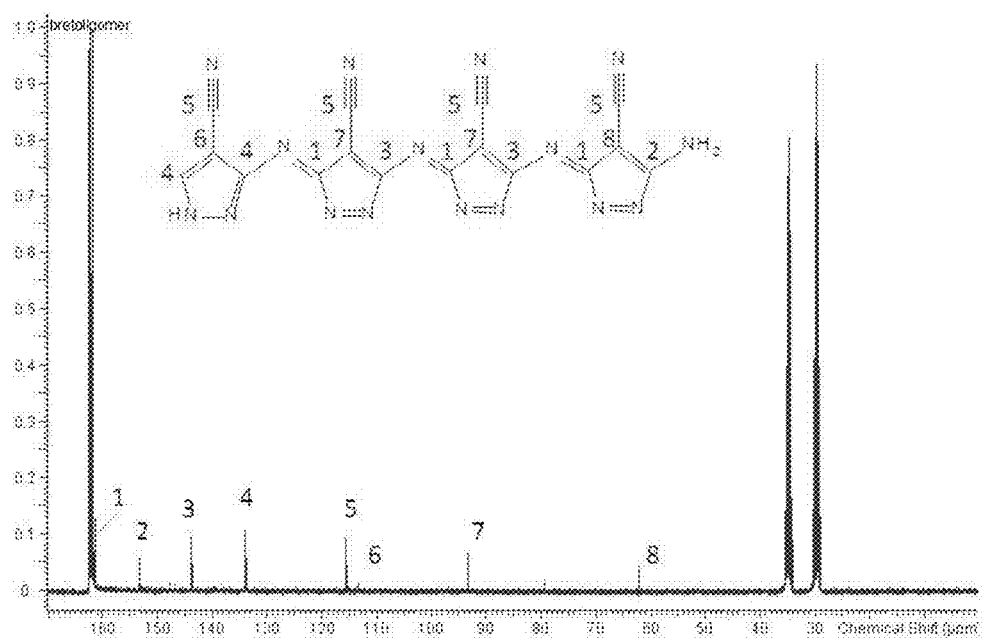
FIG. 3 illustrates $^{13}$C NMR (reference DMF-d7) of oligo (AP-CN), and proposed signal assignments for the numbered carbons.
Figure 4:
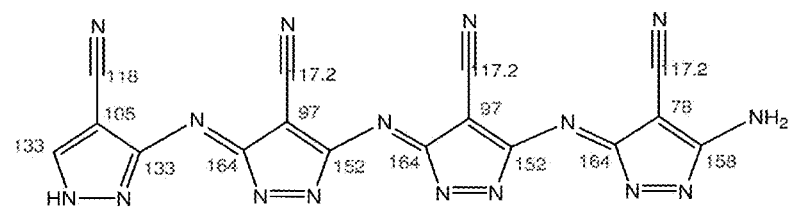
FIG. 4 illustrates $^{13}$C NMR estimation using Chem-Draw™ software.
Figure 4:
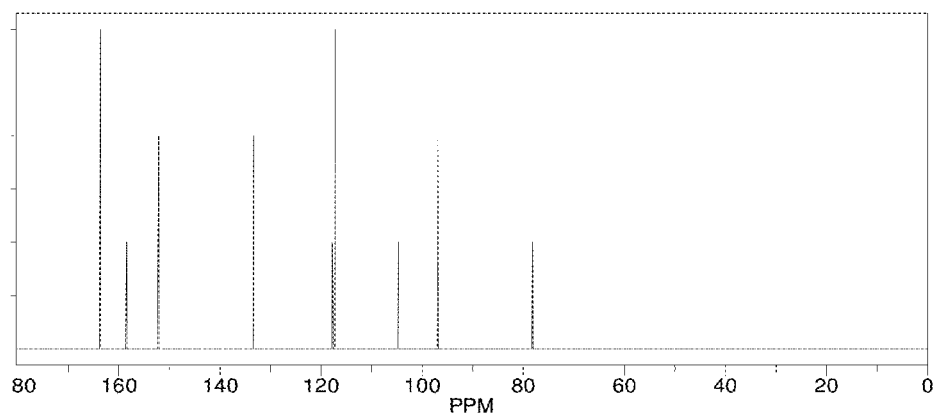

In the monomer the FTIR data shows that the carbonitrile is present without conjugation (2245 cm$^{-1}$). $^{13}$C NMR spectra (FIG. 3) shows 8 main signals, several of which correspond closely (within a few ppm) to that of software predictions (FIG. 4) for the structure. The discrepancies between software prediction and NMR data itself may arise from positive charges and variable protonation patterns in the oligomer.

Figure 5:
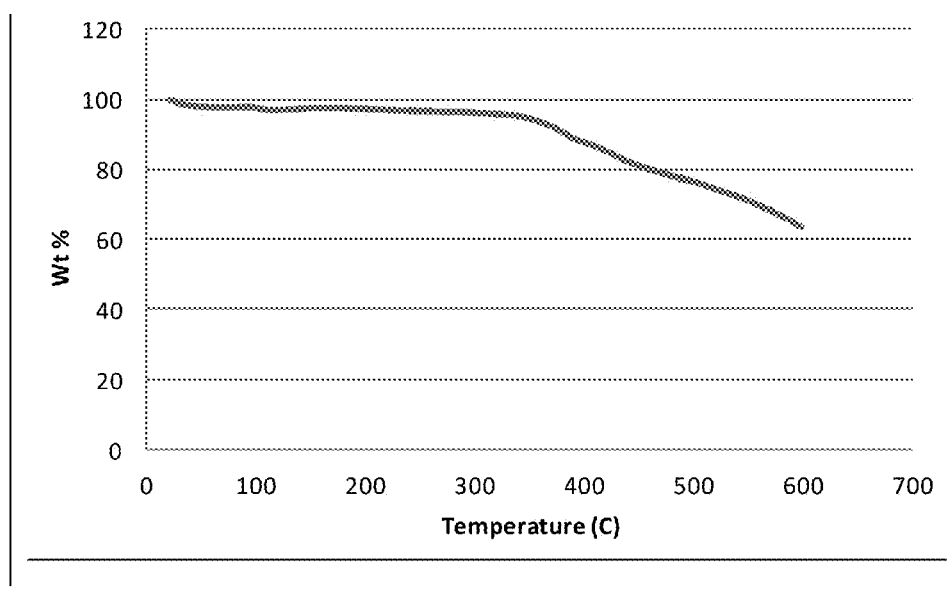
FIG. 5 illustrates Thermogravimetric analysis (TGA) of oligo(AP-CN).

Thermogravimetric studies (FIG. 5) show that the oligo (AP-CN) is thermally stable under nitrogen in the temperature range 25° C. to 360° C. (5° C./min ramp), with virtually no mass loss occurring in this range, except for water evaporation.

The oligomer undergoes gradual thermal breakdown in the range 360° C. to 600° C., losing ~30% of its mass in this range.

The high thermal stability allows it to be suitable for virtually any solar cell application.

Figure 6:
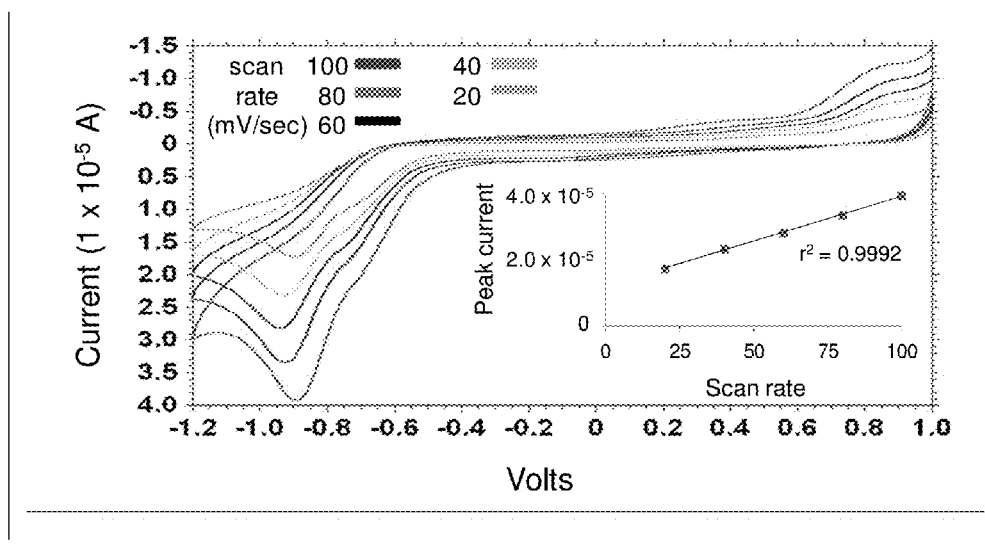
FIG. 6 illustrates Cyclic voltammetry of oligo(AP-CN), showing its reduction and oxidation processes. The Inset illustrates a linear plot of current vs. scan rate.

Electrochemically, thin films of the oligo(AP-CN) show reversible pairs of oxidation and reduction peaks at approximately +0.8 V and −1.2 V, respectively (vs. Ag wire quasi-reference, electrolyte 100 mM tetrabutylammonium hexafluorophosphate in acetonitrile, sparged and dessicated) (FIG. 6).

The plot of peak current vs. scan rate is linear, (r$^2$=0.9992), indicating that the reduction process is quasi-reversible. The reduction process results in a relatively very large peak current at −1.2 V, suggesting that the oligo(AP-CN) is an effective electron transporter.

The oligomer is electrically conductive, having resistances that are significantly lower than those reported for poly(3-amino-1,2,4 triazole) by Mert et al and Lammana et al.

Electrochemical impedance spectroscopy studies (FIGS. 13-21) showed that the oligomer can be considered to be a good electron conductor when in the reduced (n-doped) state. When partially or mostly oxidized (at 0 V or +1.2 V), the oligomer conductivity varies in a complex manner that appears to depend on location in the thin film (interfacial region or bulk).

Most conducting polymers are p-dopable (hole transporting) only, that is, they are stable charge carriers only when in a cationic state.

Oligo(AP-CN) is unusual in that as a homooligomer it can adopt both a stable n-doped (anionic) state, as shown by the reversible redox behaviors. It may be able to adopt a stable p-doped state as well. Thus it should be of interest to the electronics materials community.

Also, the subunit 3-aminopyrazole has been used in strategies for supramolecular self-assembly and polypeptide (amyloid) β-sheet stabilization.

The unusual properties of the oligomer probably arise from the multiple polar functionalities present in the repeat units.

Another desirable attribute of the oligo(AP-CN) is its simple synthesis and the low cost of the monomer. The monomer compound can be purchased in bulk for ~$2.00/gram (AK Scientific, Inc., Combi-Blocks, Inc.) In contrast, the cost of C$_{60}$ fullerene, a common electron transporting material in polymer solar cells, is ~$20.00/gram in bulk (BuckyUSA).

In the first oligo(AP-CN) synthesis the overall yield was ~60%, this can be improved by varying the reaction conditions, for example, using longer reaction times, higher temperatures, sequential removal of product, etc.

Example 1

Synthesis of Oligo(AP-CN)

The oligomer was synthesized by preparing an acidic aqueous solution ("A") with monomer and a second aqueous solution ("B") with the sodium persulfate oxidant.

Figure 7:
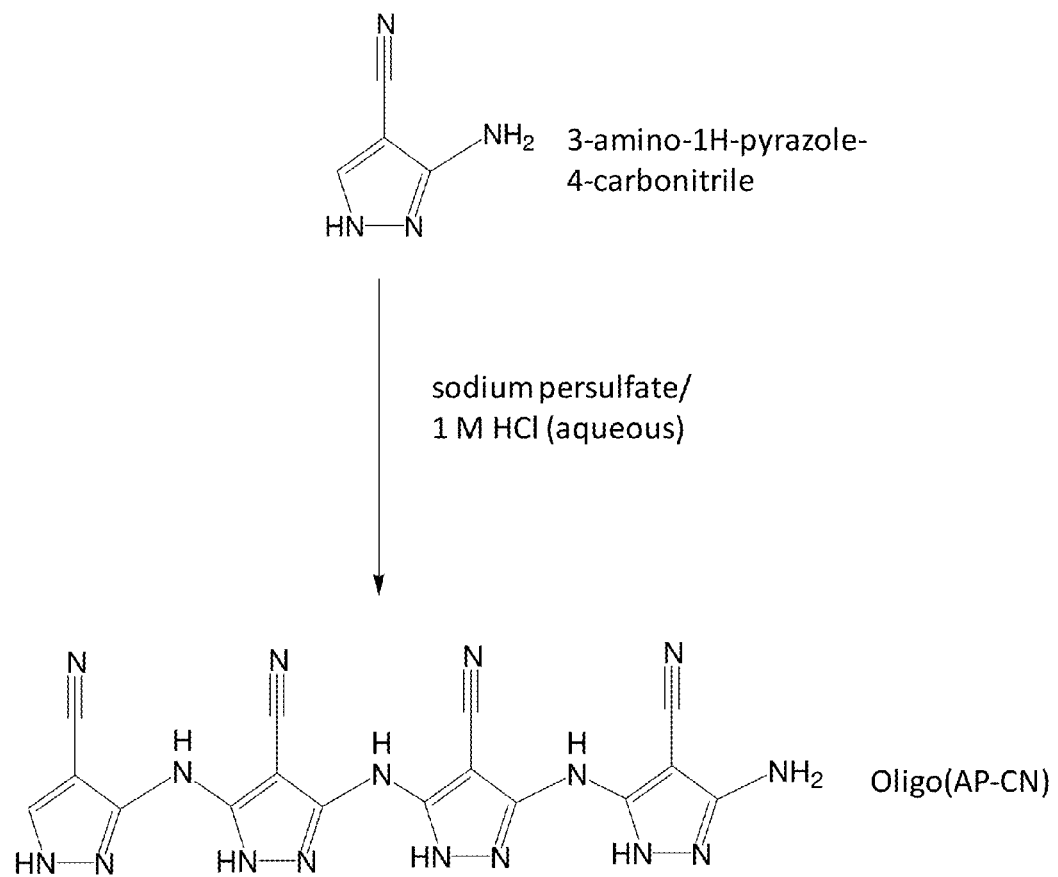
FIG. 7 illustrates Synthesis of Oligo(AP-CN).

The two solutions were then mixed, and the reaction was allowed to proceed overnight at 40° C. (FIG. 7).

Solution A was prepared using a solution of 1.6 wt % HCl in DI water, and adding monomer (3-amino-1H-pyrazole-4-carbonitrile) in the appropriate amount to form a 0.3 M solution. This corresponded to ~40 mg monomer/ml solution.

Solution B was prepared by adding ammonium persulfate (APS) to DI water in the amount to form a 0.44 M solution, corresponding to ~100 mg APS/ml solution.

The scale of the reaction was such that 1.6 g of monomer was used, in a total of 80 ml reaction volume. As the reaction proceeded with vigorous stirring at 40° C., after 1 hr it was assayed using TLC (solvent 72:10:4 ethyl acetate:methanol:water), which showed that ~15% of the monomer had converted to polymer. The reaction was allowed to proceed overnight at 40° C. By the next day, the mixture had turned brownish-grey and its pH was 1.0.

Aqueous sodium hydroxide solution was used to raise the pH of aliquots from the reaction mixture. When the pH reached 7.1, a solid precipitate formed, which was brick red. In a second aliquot, the pH was raised to 8.1 and the solution became greenish.

Centrifugation and passive precipitation gave two layers of solid—one dark green (the top layer) and one grey (the lower layer). Some yellow color remained in solution. Acetone extract of the green solid turned orange, possibly because of dissolved short oligomers. The green solid was generally insoluble in acetonitrile, methanol, methylene chloride, and ethyl acetate. It was, however, very soluble in DMF and gave a bright blue-green solution. The red solid was also found to be soluble in DMF and pyridine as well. The grey solid was soluble in methylene chloride.

The red and green solids were further purified by adding excess DI water and heating the mixture at 75° C. for 1 hour, then centrifuging the mixture and decanting the water layer, and then drying the oligo(AP-CN) overnight under vacuum at 75° C. The red and green forms of the oligomers were then characterized as described above, and their fluorescence was characterized as a function of excitation wavelength.

Oligo(AP-CN) Photocurrent Studies

In preparation for the photocurrent studies, 1.5 mg of the red oligo(AP-CN) was dissolved in 50 microliters DMF, and a 5 microliter droplet (0.5 cm diameter) was carefully deposited on gold-coated glass. The droplet was dried for 3 hrs at 75° C., forming a thin film. A second identical droplet was added on top of the film and also permitted to dry in the same manner.

In this way a mass of 0.3 mg oligomer was deposited on the coated glass.

To prepare the C$_{60}$ fullerene control, 1.5 mg fullerene was dissolved in 50 microliters o-dichlorobenzene and droplets were dried onto the coated glass as described for the oligomer. Since fullerene is often used as an electron transporter in polymer solar cells, it was chosen as a control here.

The prepared gold-coated supports were mounted into a Teflon photocell, and electrolyte solution was prepared using 100 mM sodium phosphate buffer, pH 7.1. In some cases, a sacrificial electron donor, triethanolamine, was also added at a concentration of 100 mM. The electrolyte was added to the photocell, and the working electrode was clamped to the gold-coated substrate, and the counter- and reference electrodes (Pt wire and Ag/AgCl, respectively) were immersed in the electrolyte.

To begin the photocurrent measurements the current was monitored as a function of time. The light source (a 145 W Xe lamp) was activated and allowed to shine through the electrolyte and impinge directly on the sample in the photocell—which was either the oligo(AP-CN) on the gold surface, the fullerene on the gold surface, or the bare gold surface by itself—and the resulting photocurrent was recorded. During these experiments the sample was held at either at zero voltage or at positive 0.90 V.

Figure 8:
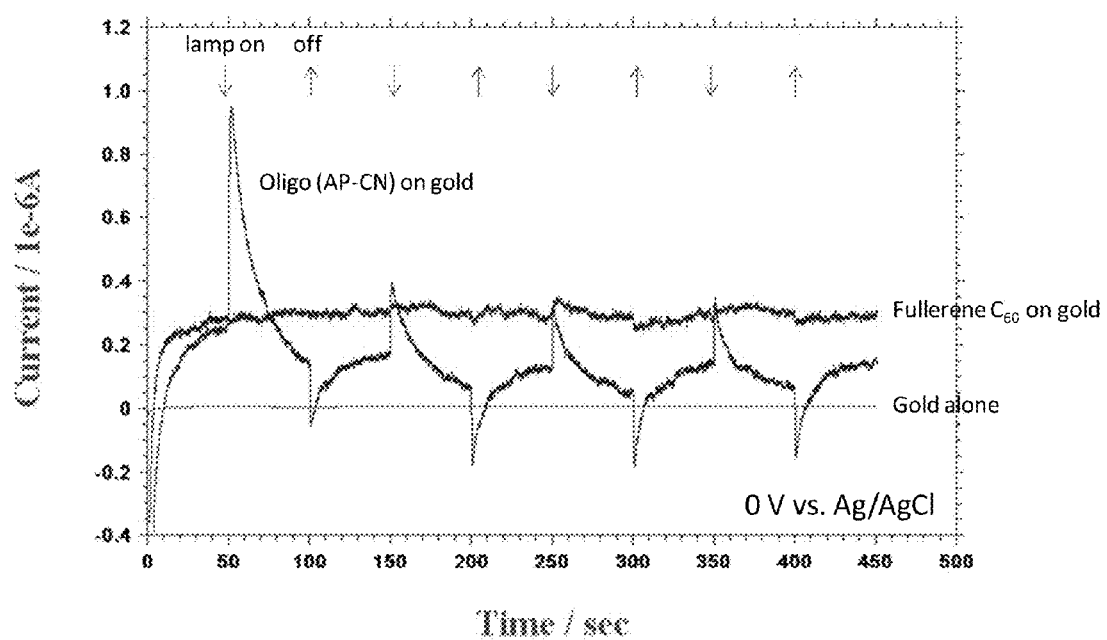
FIG. 8 illustrates Transient photocurrents generated by gold alone (red), oligo(AP-CN)/gold (blue), and fullerene/gold (brown). The sample was immersed in phosphate buffer electrolyte pH 7.1.

FIG. 8 shows the photocurrents generated by gold alone (red), oligo(AP-CN)/gold (blue), and fullerene/gold (brown) as a function of four 50-second illumination steps alternating with four 50-second periods with no illumination. The aqueous electrolyte was at pH 7.1, with no TEOA electron donor present.

The oligo(AP-CN) clearly has a much higher photocurrent than either the gold alone or the fullerene/gold.

Currents were measured relative to the lamp-off state baseline. The oligomer is able to generate peak currents of as high as nearly 1 microamp. The current in the oligomer is created nearly instantaneously, and then decays rapidly indicating that the photooxidation processes in the polymer are not immediately reversible. The bare gold surface generates virtually no photocurrent, and the fullerene yields only a very low one in later cycles.

Figure 9:
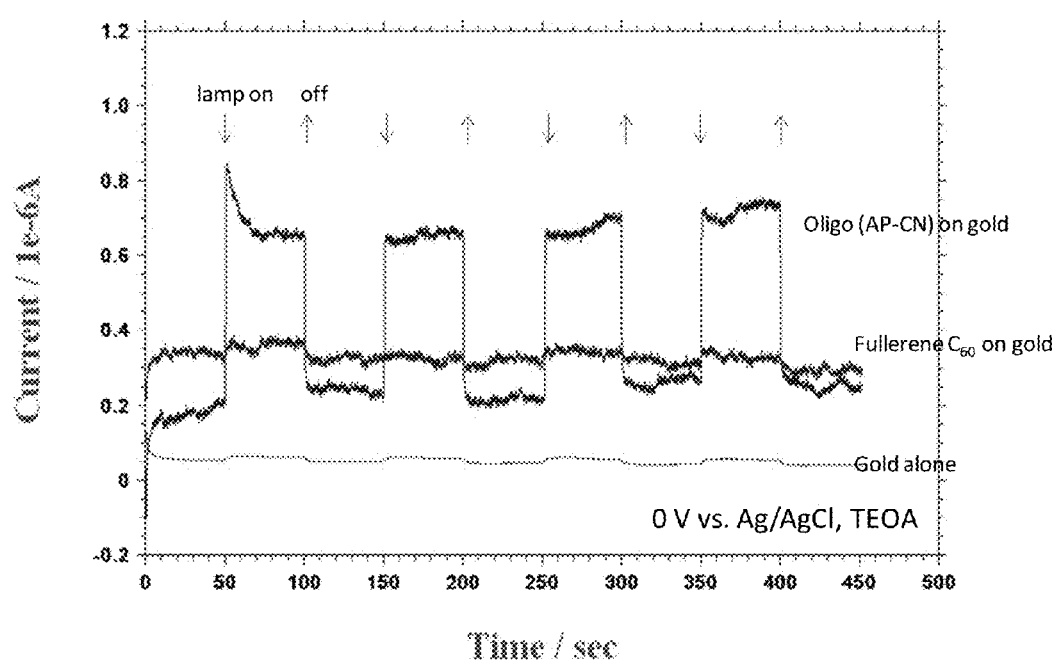
FIG. 9 illustrates Transient photocurrents generated by gold alone (red), oligo(AP-CN)/gold (blue), and fullerene/gold (brown). The sample was immersed in phosphate buffer electrolyte pH 7.1 containing 100 mM triethanolamine (TEOA), a photoactive electron donor.

FIG. 9 shows the photocurrents generated by gold alone (red), oligo(AP-CN)/gold (blue), and fullerene/gold (brown).

The sample was immersed in phosphate buffer electrolyte pH 7.1 containing 100 mM triethanolamine (TEOA), a photoactive electron donor. The same types of illumination steps used previously were used again.

Again, the oligomer/gold clearly has a much higher photocurrent than either the gold alone or the fullerene/gold, and is able to generate a peak current of ~0.8 microamps. Photooxidation of both the oligo(AP-CN) and the TEOA in solution may allow the latter to continuously regenerate the valence of the oligomer. In this manner the oligo(AP-CN) may be able to act as both an electron donor and an electron transporter.

Figure 10:
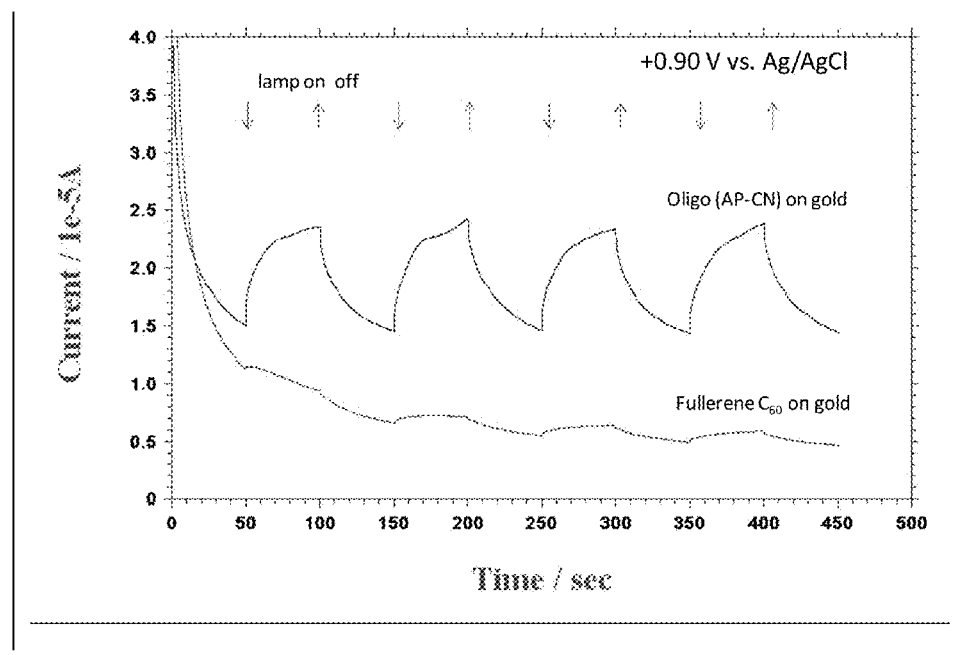
FIG. 10 illustrates Transient photocurrents generated by oligo(AP-CN)/gold (blue), and fullerene/gold (brown). The sample was immersed in phosphate buffer electrolyte pH 7.1 and held at +0.9 V vs. Ag/AgCl. No TEOA was present.

FIG. 10 shows the photocurrents generated by oligo(AP-CN)/gold (blue), and fullerene/gold (brown). The sample was immersed in phosphate buffer electrolyte pH 7.1 and held at +0.9 V vs. Ag/AgCl. No TEOA was present in this case. The same types of illumination steps used previously were used again.

Again, the oligomer/gold clearly has a much higher photocurrent than the fullerene/gold, and is able to generate a peak current of ~23 microamps. The oligomer current shows a saw tooth pattern, suggesting exponential decay processes dominated by diffusion or double-layer charge formation.

Figure 11:
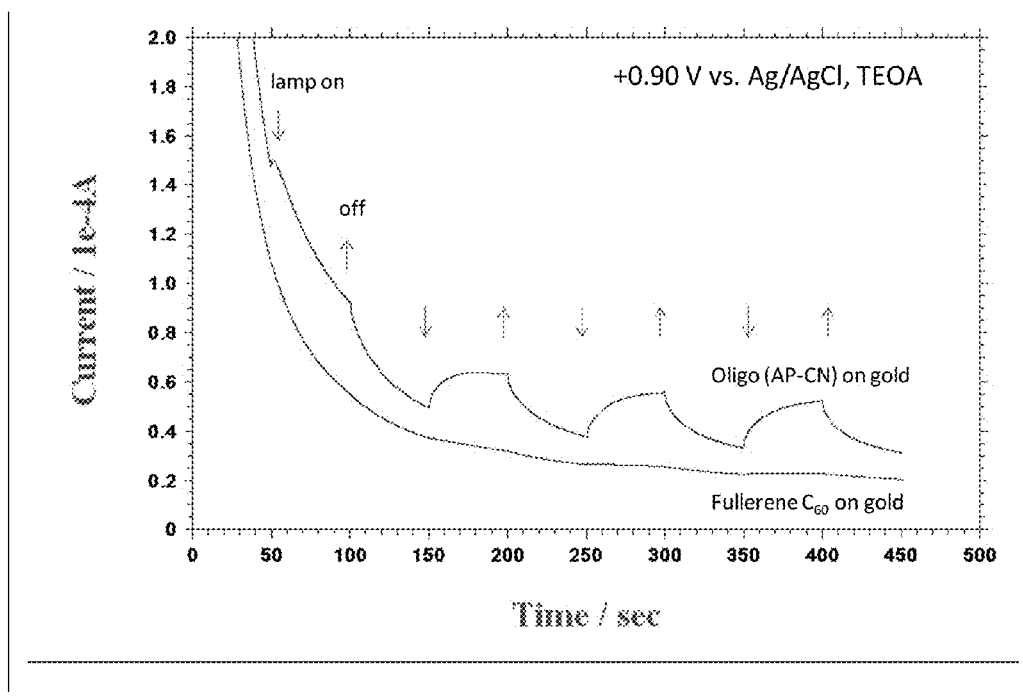
FIG. 11 illustrates Transient photocurrents generated by oligo(AP-CN)/gold (blue), and fullerene/gold (brown). The sample was immersed in phosphate buffer electrolyte pH 7.1 and held at +0.9 V vs. Ag/AgCl. TEOA was present in this case.

FIG. 11 shows the photocurrents generated by oligo(AP-CN)/gold (blue), and fullerene/gold (brown). The sample was immersed in phosphate buffer electrolyte pH 7.1 and held at +0.9 V vs. Ag/AgCl. TEOA was present in this case. The same types of illumination steps used previously were used again.

The oligomer/gold clearly has a dramatically higher photocurrent than either the gold alone or the fullerene/gold, and is able to generate a reproducible peak current of ~55 microamps, the relative highest so far.

The oligomer current again shows a saw tooth pattern, suggesting exponential decay processes dominated by diffusion or double-layer charge formation. The first cycle of the oligo(AP-CN) appears distorted, probably because of the high background current present then.

Figure 12:
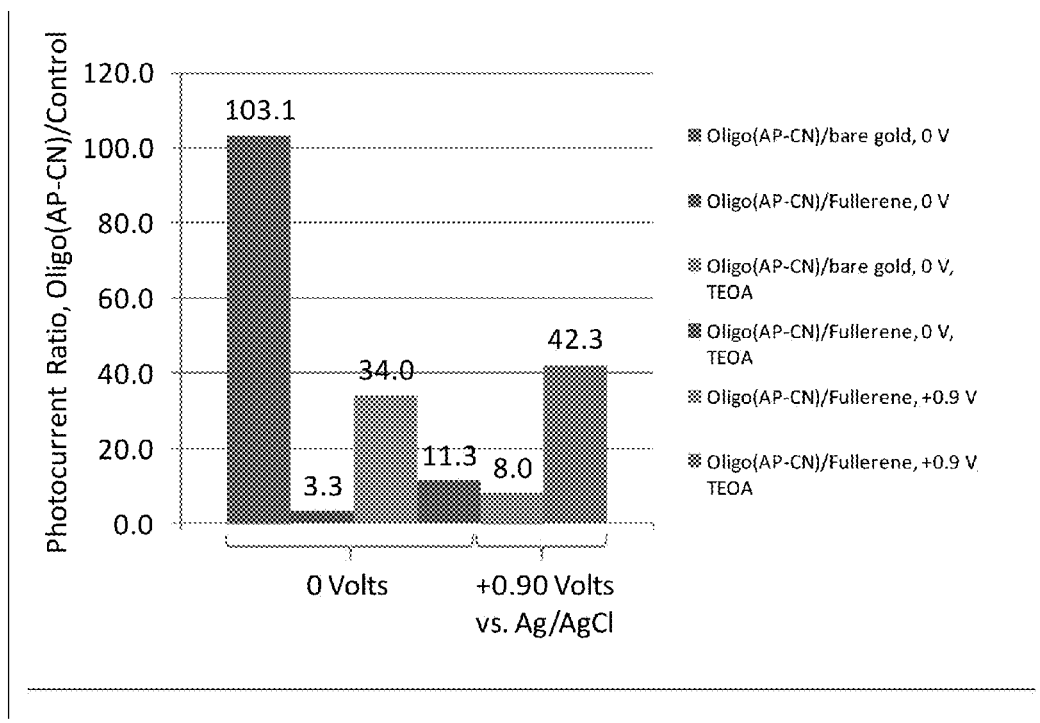
FIG. 12 illustrates Ratios of the magnitudes of the photocurrents for each material, obtained by integrating the peaks in FIGS. 7-11 and averaging over each multistep cycle.
Figure 13:
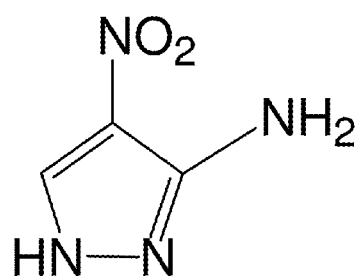
FIG. 13 illustrates (a) 4-nitro-1H-pyrazole-3-yl-amine and (b) oligo(AP-NO$_2$).
Figure 13:
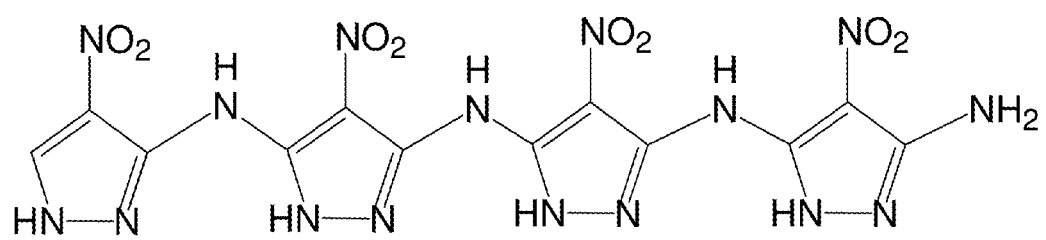

FIG. 12 gives the ratios of the magnitudes of the photocurrents for each material, obtained by integrating the peaks in FIGS. 7-11 and averaging over each multistep cycle. In the y-axis label, "control" denotes either the bare gold or fullerene/gold.

Oligo(AP-CN)/gold can generate or transport currents at levels that are 3.3 to 103 times larger than those attainable by the bare gold, and that are 8.0 to 42.3 times larger than those attainable by the fullerene/gold. At 0 volts without TEOA electron donor, the bare gold generates or carries almost no photocurrent.

In contrast, the oligomer is clearly photoactive and the fullerene appears to be slightly photoactive. Both are evidently oxidized by light, and transfer electrons to the gold layer underneath.

However, the oligomer accomplishes this in a much better-defined process (FIG. 8) that shows nearly instantaneous current generation upon irradiation (followed by an exponential decay), and gives current at a level that is 3.3 times higher. The fullerene-generated current is formed in a process that is much less clearly defined or consistent. At 0 volts with TEOA electron donor, the bare gold generates or carries a very small amount of photocurrent (FIG. 9).

Again, the oligomer is definitely photoactive, again showing nearly instantaneous current generation upon irradiation with steady maintenance over the irradiation time, giving currents that are 34-fold and 11 fold times higher than the bare gold and fullerene/gold, respectively. The fullerene-generated current is again formed in a process that is much less clearly defined or consistent. At +0.9 volts with no TEOA electron donor (FIG. 10) the oligomer is again definitely photoactive, this time showing a positive exponential current generation upon irradiation with a negative exponential response when the illumination is stopped. Its photocurrent is 8-fold (+0.9 V, no TEOA) and 42.3-fold (+0.9 V, TEOA) higher than the fullerene/gold, respectively. When immersed in electrolyte, the bare gold surface began to oxidize when subjected to +0.9 V so it was not used as a comparison here. For both the oligo(AP-CN) and C60 fullerene materials, both the background currents and photocurrents are much higher than in the cases with no applied voltage.

Example 2

Synthesis of Oligo(AP-NO$_2$)

The oligomerization chemistry used for the formation of 3-amino-1H-pyrazole-4-carbonitrile was extended to a second monomer, 4-nitro-1H-pyrazole-3-yl-amine, as illustrated in FIG. 12(a).

Here, the carbonitrile is replaced by a nitro group. This monomer was synthesized in-house.

The material is oligomerized at 40° C. in a straightforward one-step process corresponding to that used above for oligo(AP-CN).

Electrochemical studies show that this material (oligo(4-nitro-1H-pyrazole-3-yl-amine), or "oligo(AP-NO$_2$)") can adopt an n-doped state (and a p-doped state), as can oligo (AP-CN), as discussed below.

Electrochemical Impedance Spectroscopy

For electrochemical characterization of both oligomers we used electrochemical impedance spectroscopy (EIS), which measures the electronic response of the material as it is subjected to alternating currents of variable frequencies ranging from MHz to sub-Hz. This method is quite powerful in that it can reveal material processes that have a wide range of time constants, and simultaneously provide measurements of various types of resistances, capacitive effects, inductive effects, material heterogeneity, ion diffusivities in the bulk of the material, and other phenomena.

For both oligomers, the equivalent circuit models (FIG. 19) were constructed using resistors, capacitors, Warburg elements, and constant phase elements. The latter two types of elements will be defined below. Each model has a certain error associated with it. For the oligo(AP-CN), the percentage error ranged from 1.7% to 4.3%; for the oligo(AP-NO$_2$), it ranged from 1.7% to 3.2%. The numerical values for the elements in the circuit models are given in Table 1.

Each oligomer has 3 Nyquist plots describing it, one for each voltage investigated (−1.2 V, 0 V, +1.2 V). These are presented in FIGS. 14-19. The Nyquist diagram represents the capacitive component of the impedance (−Z") plotted versus the resistive component (Z').

Figure 14:
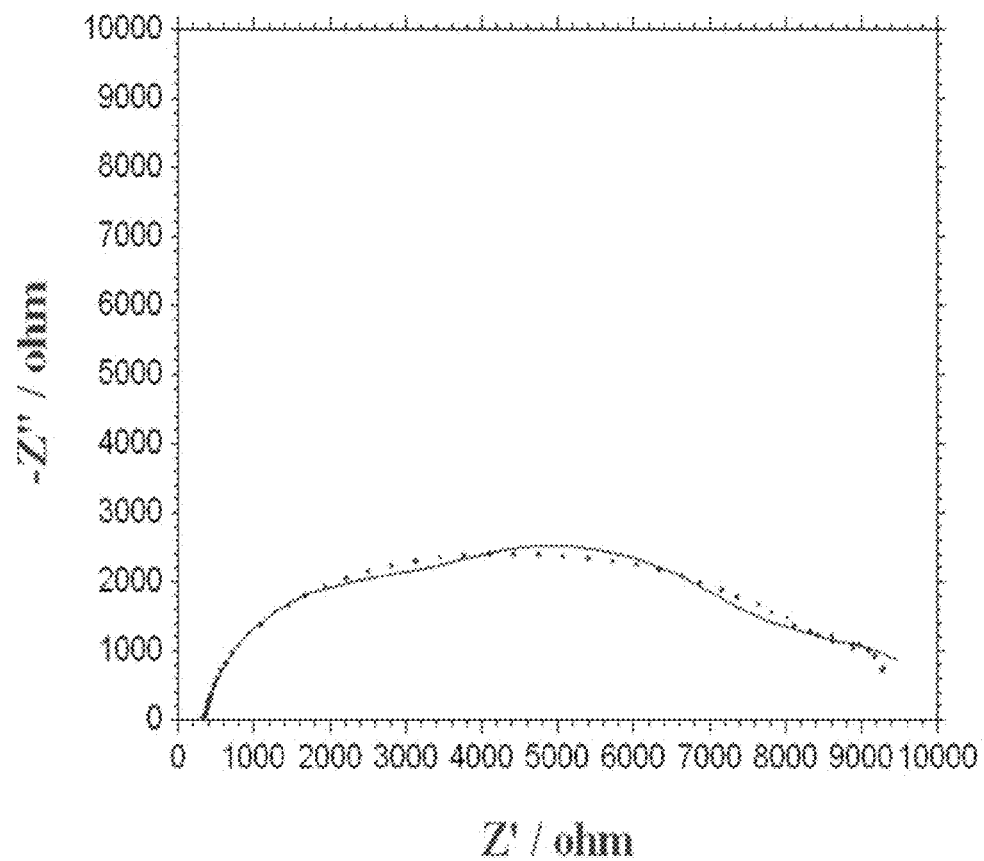
FIG. 14 illustrates a Nyquist plot for oligo(AP-CN) held at −1.2 V vs. Ag wire quasi-reference. Red circles=data, blue line=circuit fit. Fit error=2.1%.
Figure 15:
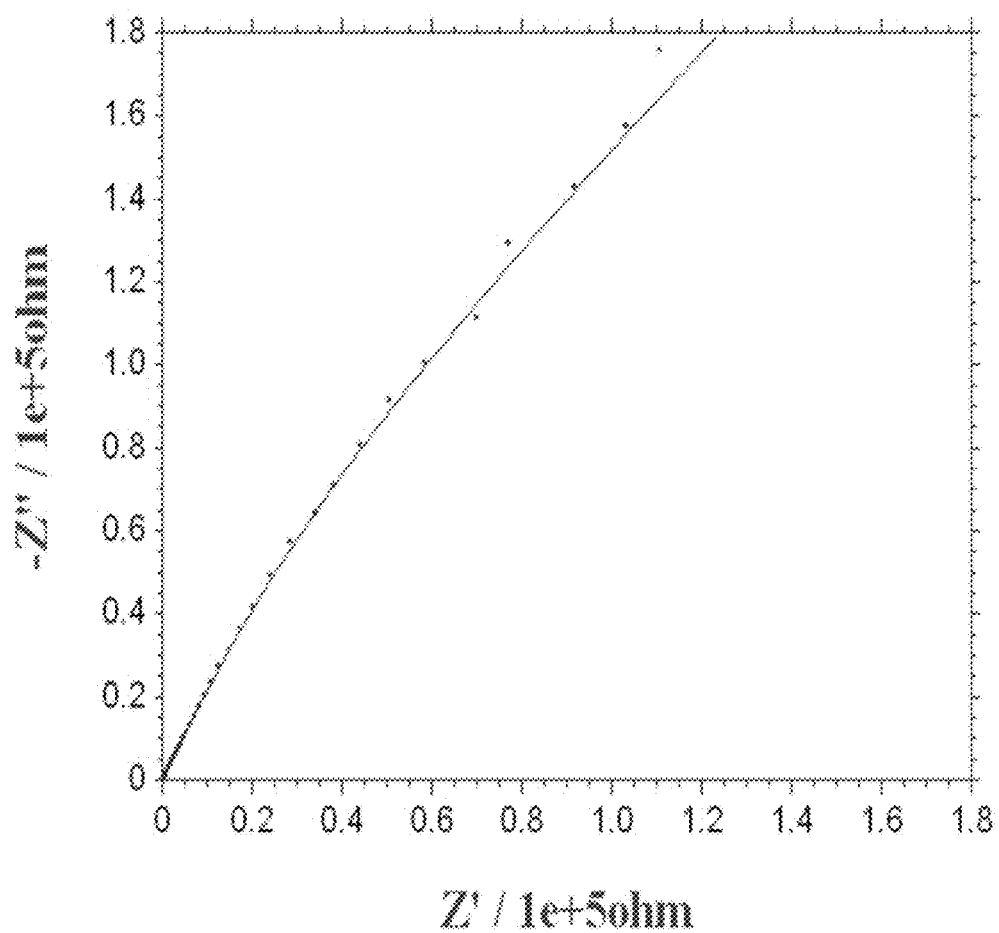
FIG. 15 illustrates a Nyquist plot for oligo(AP-CN) held at 0 V vs. Ag wire quasi-reference. Error=1.7%.
Figure 16:
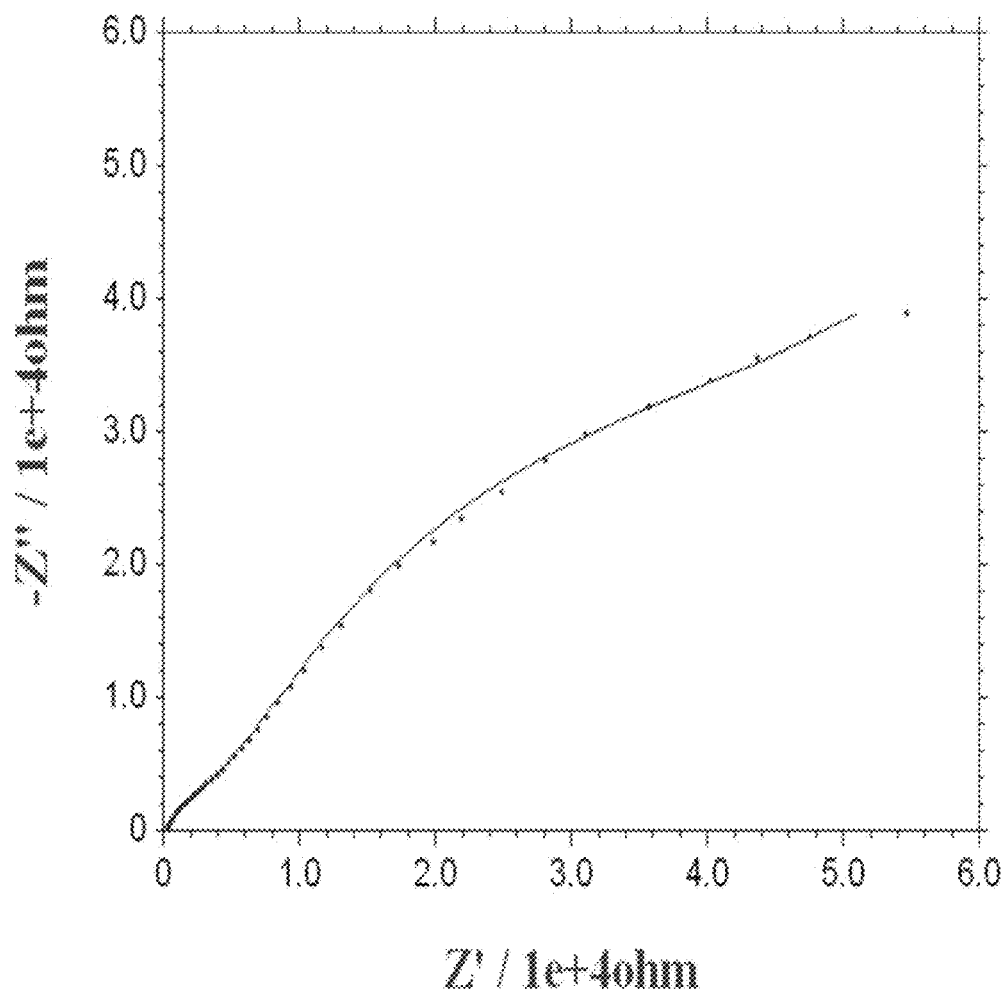
FIG. 16 illustrates a Nyquist plot, oligo(AP-CN) held at −1.2 V vs. Ag wire quasi-reference. Error=1.7%.
Figure 17:
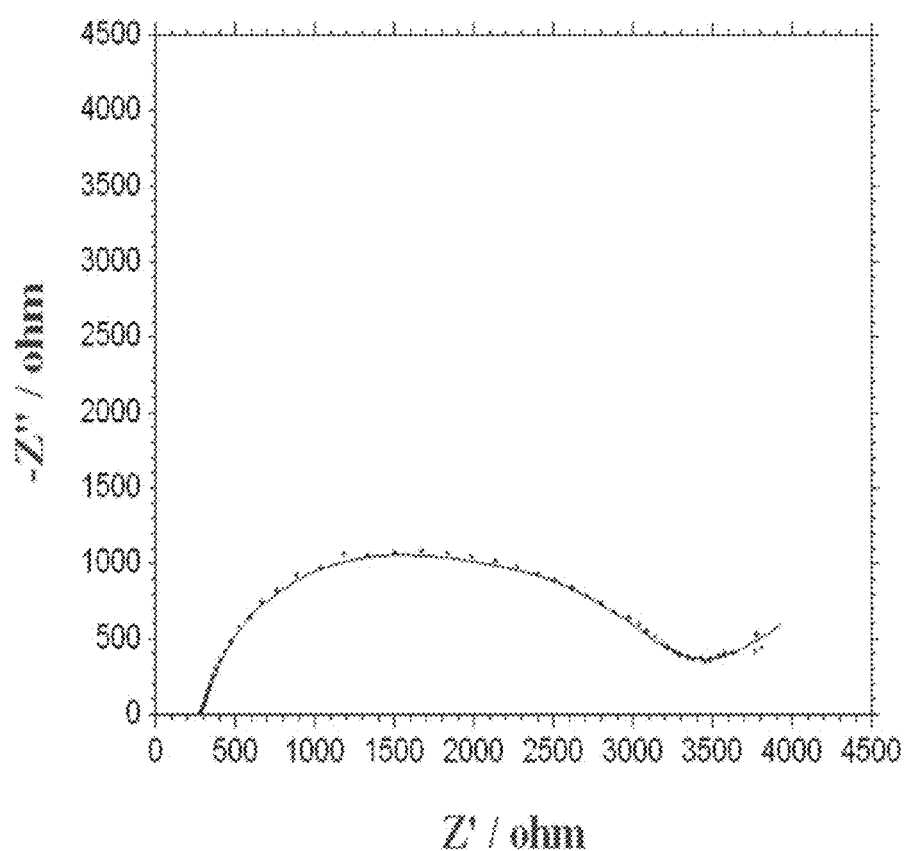
FIG. 17 illustrates a Nyquist plot for oligo(AP-NO$_2$) held at −1.2 V vs. Ag wire quasi-reference. Red circles=data, blue line=circuit fit. Error=1.8%
Figure 18:
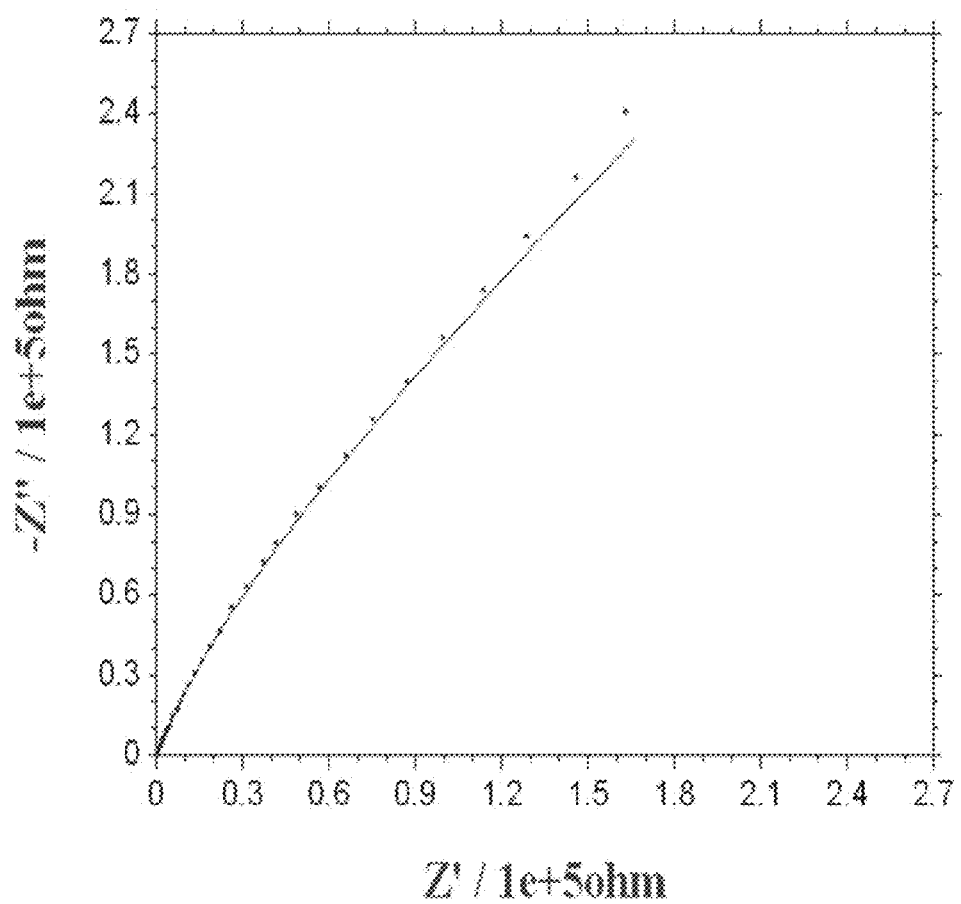
FIG. 18 illustrates a Nyquist plot, oligo(AP-NO$_2$) held at 0 V vs. Ag wire quasi-reference. Error=1.7%.
Figure 19:
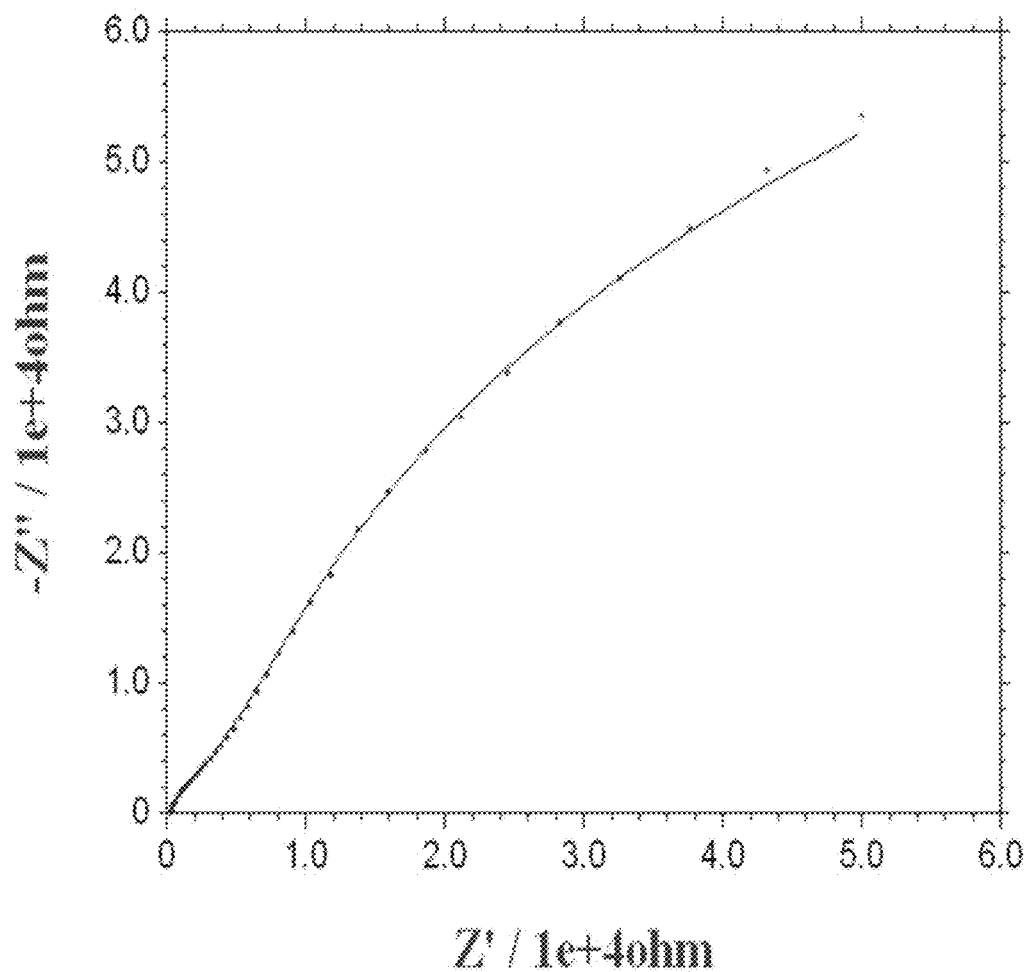
FIG. 19 illustrates a Nyquist plot, oligo(AP-NO$_2$) held at +1.2 V vs. Ag wire quasi-reference. Error=3.2%.
Figure 20:
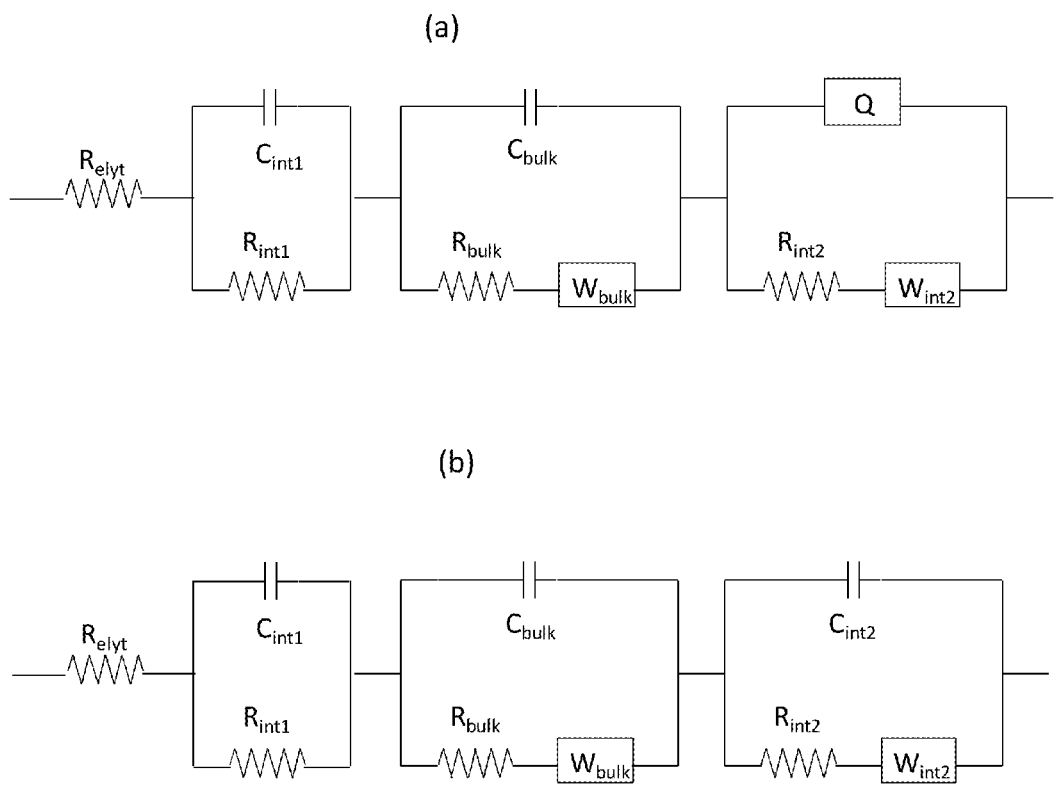
FIG. 20 illustrates equivalent circuits for the oligomers at −1.2 V (top) and at 0 V or +1.2 V (bottom).
Figure 21:
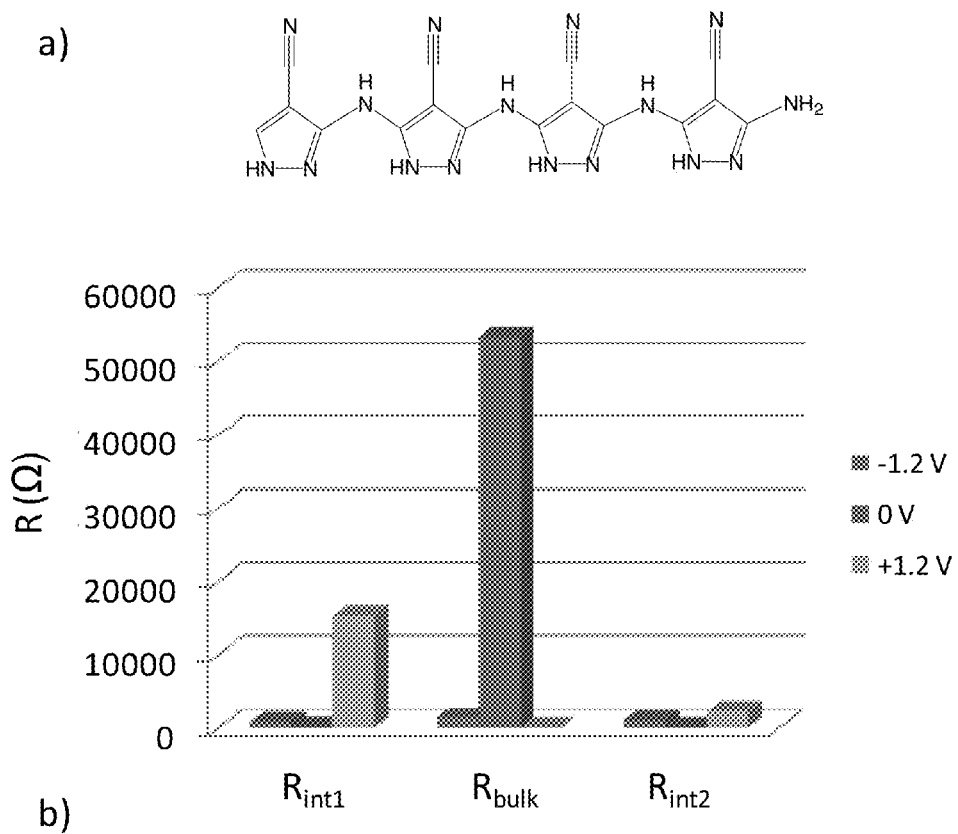
FIG. 21 illustrates a structure (a), electrical resistances (b) and Warburg coefficients (diffusion resistances) of oligo(AP-CN) (c). Percent error for the circuit elements ranges from 1.7% to 4.3%.
Figure 21:
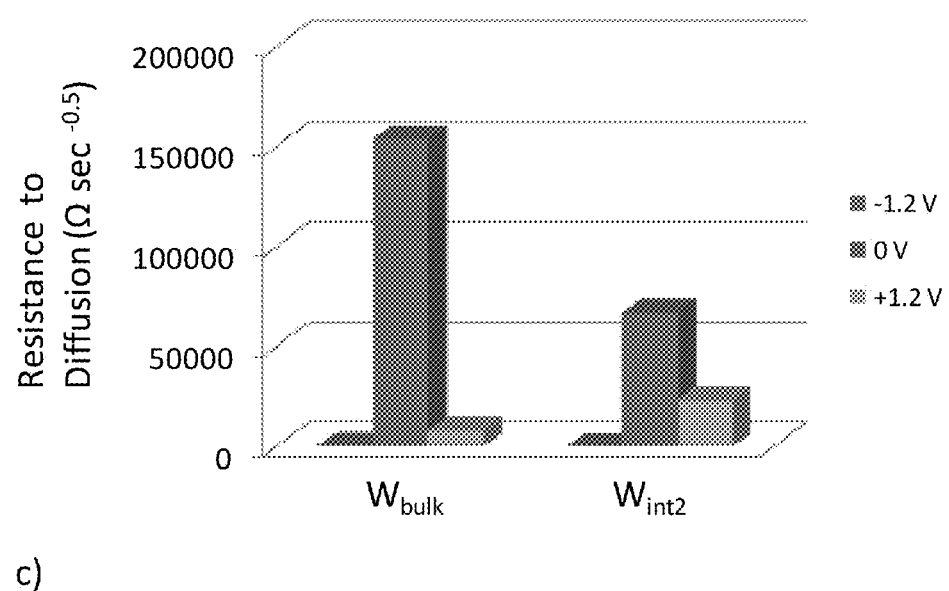
Figure 22:
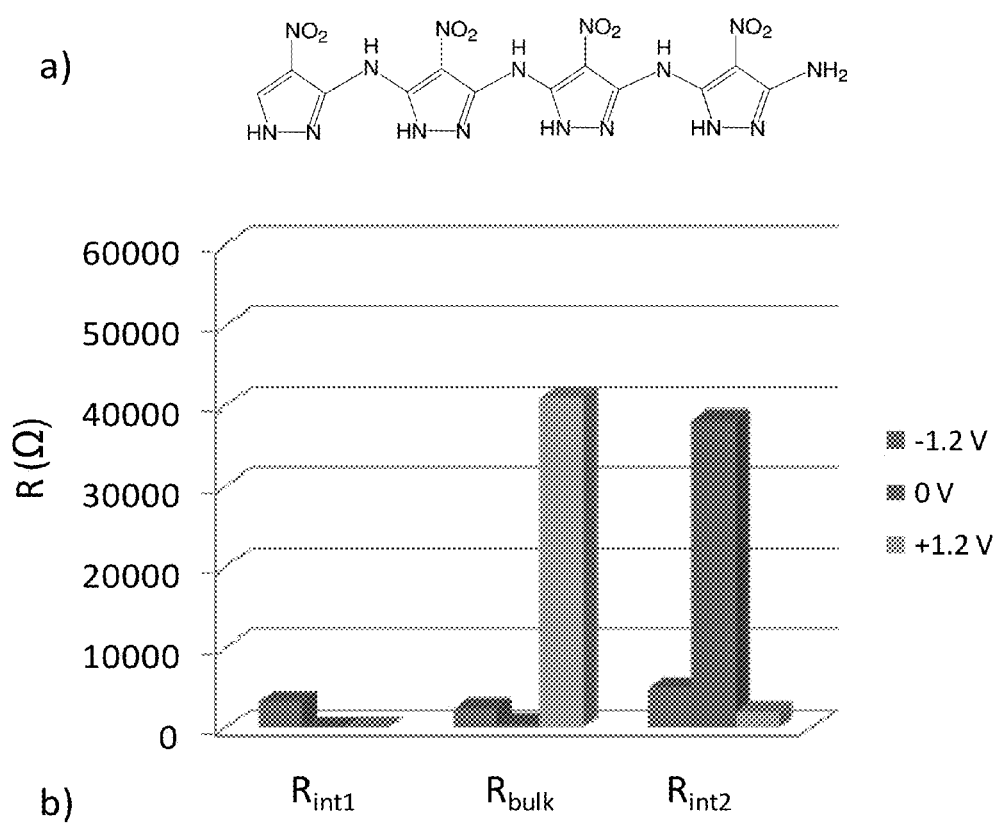
FIG. 22 illustrates a structure (a), electrical resistances (b) and Warburg coefficients (diffusion resistances) of oligo(AP-CN) (c). Percent error for the circuit elements ranges from 1.7% to 3.2%.
Figure 22:
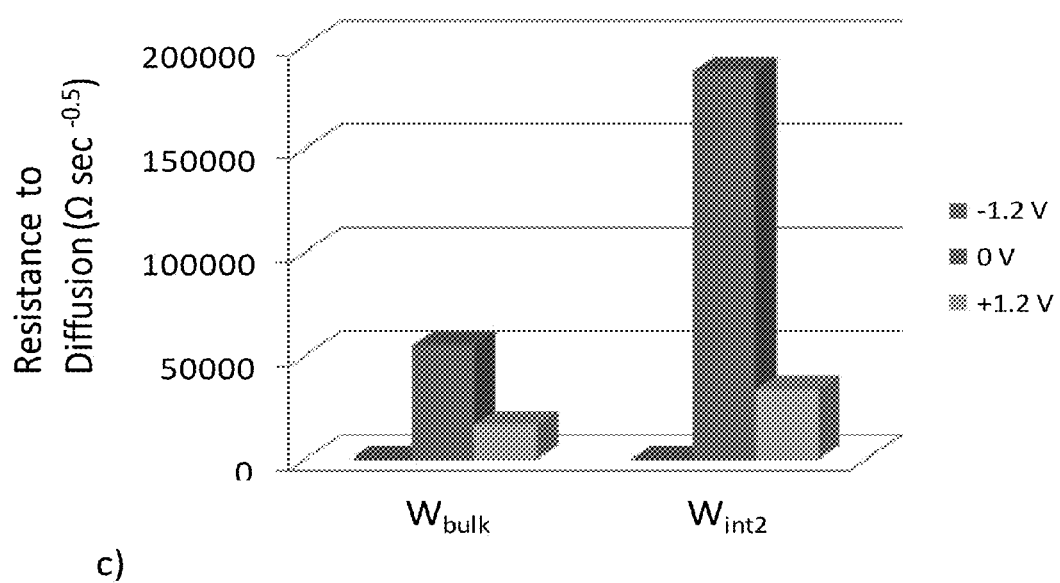

In the plots, the measured impedance response data of the material is represented as red circles and the impedance of the chosen circuit model is represented as a blue trace. FIGS. 14-15 give the Nyquist plots for oligo(AP-CN), FIGS. 17-19 give them for oligo(AP-NO$_2$).

The equivalent circuits (FIG. 19) contain an initial resistor that accounts for electrolyte resistance (R$_{elyte}$), followed sequentially by three parallel segments. The first segment contains a capacitor in parallel with an interfacial charge-transfer resistance R$_{int1}$.

For both oligomers, this resistance is relatively low, generally in the $\Omega$ to few k$\Omega$ range (FIG. 20, Table 1), with the highest value for the oligo(AP-CN) when the material is held at +1.2 V. The capacitances in the first segment are all relatively small, ranging from $10^{-5}$ to $10^{-7}$ Farads (F).

The second parallel segment contains a resistor R$_{bulk}$ in parallel with a capacitor C$_{bulk}$. The subscript bulk denotes the inner region of the oligomer film, away from the interfaces. In this region, R$_{bulk}$ is relatively very low for the oligo(AP-CN) at −1.2 V (1440$\Omega$) and +1.2 V (42$\Omega$).

This is one indication that the oligomer is able to adopt both an n-doped (reduced) and p-doped (oxidized) states. However, R$_{bulk}$ is much higher at 0 V (5.33×10$^4$$\Omega$), because in that state the material may contain mixtures of doping conditions that do not conduct either negative or positive charges effectively. The situation is different, however, for the oligo(AP-NO$_2$) for which R$_{bulk}$ is low at −1.2 V (2382$\Omega$) and 0 V (521$\Omega$), but relatively high at +1.2 V (4.1×10$^4$$\Omega$). This oligomer appears to switch into a rather more semi-conducting vs. conducting state at oxidizing voltages, whereas oligo(AP-CN) shows this behavior at 0 V.

The R$_{bulk}$ is in series with a Warburg impedance W$_{bulk}$, which represents the resistance that is encountered by long range diffusion processes in this inner region. For both the oligo(AP-CN) and the oligo(AP-NO$_2$), the magnitude of W is much smaller when the material is held at −1.2 V and +1.2 V, versus when at 0 V. Its smallest values are 0.76 and 447 $\Omega$sec$^{-0.5}$ for the oligo(AP-CN) and oligo(AP-NO$_2$), respectively, at −1.2 V. This is probably because the applied voltage is increasing charge diffusion rates. It may also be because in the reduced state the electron-rich oligomer chains repel one another, causing the nanoporosity to increase and permit rapid diffusion. However, the largest values are 1.54×10$^5$ $\Omega$sec$^{-0.5}$ and 5.48×10$^4$ $\Omega$sec$^{-0.5}$ for the two films when at 0 V. This may occur because in the neutral state the oligomers can pi-stack to increase the density of the material and thus slow diffusion. At +1.2 V, the W$_{bulk}$ values decrease substantially to 7.80×10$^3$ $\Omega$sec$^{-0.5}$ and 1.70×10$^4$ $\Omega$sec$^{-0.5}$, respectively. As above, this is probably because the applied voltage is increasing charge diffusion rates. It may also be because in the oxidized state the oligomers may enter a quinoid rigid-rod (vs. aromatic flexible rod) form, which can be conductible to a higher nanoporosity and thus rapid diffusion. Alternatively, simple like-charge repulsion between oligomer chains may result in a higher nanoporosity. For both oligomers, the capacitance values are small, in the range $10^{-6}$ to $10^{-7}$ F.

The third parallel circuit segment contains a resistor R$_{int2}$ in parallel with either a capacitor C$_{int2}$, or a constant phase element (CPE). The subscript "int2" designates the interface between the oligomer layer and the electrode (glassy carbon). CPEs are used extensively in equivalent circuit models. They can represent distributed (heterogeneous) surface reactivity or morphology, roughness or fractal geometry, or material porosity. The CPE can also model a simple electrical double layer. When the oligomers are at −1.2 V, a CPE was used in the circuit model because it gave the best fit to the data. The units for a CPE are $\Omega^{-1}$ s$^n$ where 0<n<1. For the oligomers at 0 V and +1.2 V, a capacitor is used since it gave the best fit.

The R$_{int2}$ values for the oligo(AP-CN) are relatively low at all voltages (1032$\Omega$, 61$\Omega$, and 2266$\Omega$ for −1.2 V, 0 V and +1.2 V). This suggests that the oligomer that is very near the carbon electrode may be organized in some fashion as to give a high charge mobility for both electrons and positively-charged centers. The surface of the glassy carbon may assist in short and long-range ordering processes. For the oligo(AP-NO$_2$), the R$_{int2}$ values are relatively low at −1.2 V and +1.2 V (4950$\Omega$ and 1892$\Omega$). However, the resistance is much higher at 0 V (3.82×10$^4$$\Omega$). This may be because the oligomer near the electrode surface may be organized in a fashion that lowers its conductivity, unless a potential is applied.

The R$_{int2}$ is in series with a Warburg impedance W$_{int2}$, which represents the resistance that is encountered by long range diffusion processes in this interfacial region. For both the oligo(AP-CN) and the oligo(AP-NO$_2$), the magnitude of W$_{int2}$ is much smaller when the material is held at −1.2 V and +1.2 V, versus when at 0 V. Its smallest values are 0.78 and 0.74 $\Omega$sec$^{-0.5}$ for the oligo(AP-CN) and oligo(AP-NO$_2$), respectively, at −1.2 V. As was the case for W$_{int1}$, this is probably because the applied voltage is increasing charge diffusion rates. Also, in a trend similar to that of W$_{int1}$, the largest values (~1×10$^5$ $\Omega$sec$^{-0.5}$) occur when the oligomers are at 0 V, probably because pi-stacking increases the density of the material. At +1.2 V, the values decrease to 2.33 and 3.38×10$^4$ $\Omega$sec$^{-0.5}$ likely for the same reasons mentioned above for W$_{int1}$.

Both oligomers show capacitances in the relatively low range of ~10$^{-6}$ to 10$^{-7}$ F. Thus, most of the observed impedance arises from the resistor and Warburg elements. For both materials at −1.2 V, it is of interest that the CPE models the second interface more closely than does a capacitor. The CPEs have a value of 1.01×10$^{-4}$ to 1.4×10$^{-4}$ $\Omega^{-1}$ s$^n$, which may indicate that both materials experience an increased heterogeneity when the reducing voltage is applied.

From this discussion, one can conclude that both oligomers are can be considered to be good electron conductors when in the reduced (n-doped) state. This is evidenced by the low values for the R and W circuit elements. When partially or mostly oxidized (at 0 V or +1.2 V), the oligomer conductivity varies in a complex manner that appears to depend on location (interfacial region or bulk). The high electron conductivity quantified by the EIS is consistent with the observations of the large photocurrents supported by the oligo(AP-CN).

TABLE 1

Circuit elements and values.

| | Oligo(AP-CN) | | | Oligo(AP-NO$_2$) | | |
|---|---|---|---|---|---|---|
| | −1.2 V | 0 V | +1.2 V | −1.2 V | 0 V | +1.2 V |
| $R_{int1}$ (Ω) | 741 | 25 | $1.53 \times 10^4$ | 3167 | 40 | 50.8 |
| $R_{bulk}$ (Ω) | 1440 | $5.33 \times 10^4$ | 42 | 2382 | 521 | $4.09 \times 10^4$ |
| $R_{int2}$ (Ω) | 1032 | 61 | 2266 | 4950 | $3.82 \times 10^4$ | 1892 |
| $W_{bulk}$ (Ωsec$^{-0.5}$) | 447 | $1.54 \times 10^5$ | 7797 | 0.759 | $5.48 \times 10^4$ | $1.70 \times 10^4$ |
| $W_{int2}$ (Ωsec$^{-0.5}$) | 0.777 | $6.67 \times 10^4$ | $2.33 \times 10^4$ | 0.748 | $1.87 \times 10^5$ | $3.38 \times 10^4$ |
| $C_{int1}$ (F) | $8.66 \times 10^{-6}$ | $6.20 \times 10^{-7}$ | $1.49 \times 10^{-5}$ | $5.03 \times 10^{-6}$ | $4.69 \times 10^{-7}$ | $6.62 \times 10^{-7}$ |
| $C_{bulk}$ (F) | $9.40 \times 10^{-7}$ | $2.81 \times 10^{-6}$ | $1.20 \times 10^{-7}$ | $8.85 \times 10^{-7}$ | $4.87 \times 10^{-7}$ | $8.12 \times 10^{-6}$ |
| $C_{int2}$ (F) | — | $4.26 \times 10^{-7}$ | $8.54 \times 10^{-7}$ | — | $1.89 \times 10^{-6}$ | $6.89 \times 10^{-7}$ |
| Q (Ω$^{-1}$s$^n$) | $1.19 \times 10^{-4}$ | — | | $1.01 \times 10^{-4}$ | — | |
| Fit error | 2.1% | 1.7% | 4.3% | 1.8% | 1.7% | 3.2% |

The oligomers are highly effective electron transporters (n-dopable). There are relatively few other types of organic, electrically conducting oligomers that have this capability. The oligomers are also be p-dopable, that is, they are also able to transport "holes" (positively-charged centers). They are easy to synthesize, and use inexpensive starting materials. They have a high thermal stability and are thus suitable for incorporation into solar cells. They are soluble in common polar organic solvents and are thus easily processable.

Both oligomers have an electron-withdrawing group at the 4-position of the pyrazole ring. Oligo(AP-CN) has a carbonitrile group (C-triple bond-N) located there, whereas oligo(AP-NO$_2$) has a nitro group (NO$_2$). Other types of electron-withdrawing groups (such as trifluoromethyl, perfluoroalkane, halogen, aldehyde, ketone, ester, carboxylate, sulfonate, ammonium, quaternary amine) can be introduced there, and that oligomers formed from the resulting monomer have properties similar to oligo(AP-CN) and oligo(NO$_2$).

Many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What we claim is:

1. An electrically conducting organic oligomer comprising 4-nitro-1H-pyrazole-3-yl-amine, 4-trifluoromethyl-1H-pyrazol-3-yl-amine, 4-trichloromethyl-1H-pyrazol-3-yl-amine, 4-tribromomethyl-1H-pyrazol-3-yl-amine, 4-ammonium-1H-pyrazol-3-yl-amine, 4-trimethylammonium-1H-pyrazol-3-yl-amine, 4-triethylammonium-1H-pyrazol-3-yl-amine, or 4-tripropylammonium-1H-pyrazol-3-yl-amine.

* * * * *